United States Patent [19]

Bonham et al.

[11] Patent Number: 5,496,504
[45] Date of Patent: Mar. 5, 1996

[54] HALOMETHYL-1,3,5-TRIAZINES CONTAINING A MONOMERIC MOIETY

[75] Inventors: James A. Bonham; Mitchell A. Rossman; Richard J. Grant, all of St. Paul, Minn.

[73] Assignee: Minnesota Mining and Manufacturing Company, St. Paul, Minn.

[21] Appl. No.: 345,594

[22] Filed: Nov. 28, 1994

Related U.S. Application Data

[62] Division of Ser. No. 49,555, Apr. 19, 1993, Pat. No. 5,387,682, which is a continuation of Ser. No. 555,301, Jul. 18, 1990, abandoned, which is a continuation-in-part of Ser. No. 241,691, Sep. 7, 1988, abandoned.

[51] Int. Cl.$^6$ ..................... G03C 1/00
[52] U.S. Cl. ..................... 252/600
[58] Field of Search ..................... 252/600

[56] References Cited

U.S. PATENT DOCUMENTS

| | | | |
|---|---|---|---|
| 3,495,987 | 2/1970 | Moore | 430/288 |
| 3,617,288 | 11/1971 | Hartman et al. | 430/70 |
| 3,640,718 | 2/1972 | Smith | 430/270 |
| 3,644,300 | 2/1972 | Dorfman et al. | 260/78.4 N |
| 3,652,464 | 3/1972 | Grindahl et al. | 260/2 R |
| 3,652,561 | 3/1972 | Dexter | 544/219 |
| 3,779,778 | 12/1973 | Smith et al. | 430/270 |
| 3,847,916 | 11/1974 | Kim et al. | 260/248 CS |
| 3,905,815 | 12/1975 | Bonham | 430/156 |
| 3,954,475 | 5/1976 | Bonham et al. | 96/67 |
| 3,987,037 | 10/1976 | Bonham et al. | 544/216 |
| 4,181,752 | 1/1980 | Martens et al. | 427/516 |
| 4,189,323 | 2/1980 | Buhr | 430/281 |
| 4,239,850 | 12/1980 | Kita et al. | 430/281 |
| 4,259,432 | 3/1981 | Kondoh et al. | 430/281 |
| 4,391,687 | 7/1983 | Vesley | 525/330.5 |
| 4,476,215 | 10/1984 | Kausch | 430/281 |
| 4,505,793 | 3/1985 | Tamoto et al. | 204/159.16 |
| 4,758,497 | 7/1988 | Shah et al. | 430/193 |
| 4,820,607 | 4/1989 | Aoai | 430/190 |
| 4,826,753 | 5/1989 | Higashi et al. | 430/281 |
| 4,933,452 | 6/1990 | White et al. | 544/204 |
| 5,194,610 | 3/1993 | Hamprecht | 544/219 |
| 5,368,783 | 11/1994 | Kobayashi et al. | 252/600 |

FOREIGN PATENT DOCUMENTS

| | | |
|---|---|---|
| 510525 | 3/1955 | Canada . |
| 639182 | 4/1962 | Canada . |
| 639181 | 4/1962 | Canada . |
| 767644 | 9/1967 | Canada . |
| 882130 | 9/1971 | Canada . |
| 882138 | 9/1971 | Canada . |
| 986512 | 3/1976 | Canada . |
| 0109291 | 5/1984 | European Pat. Off. . |
| 0305115 | 3/1989 | European Pat. Off. . |
| 0341720 | 11/1989 | European Pat. Off. . |
| 0359431 | 3/1990 | European Pat. Off. . |
| 0359430 | 3/1990 | European Pat. Off. . |
| 2851641 | 5/1979 | Germany . |
| 3517440 | 11/1985 | Germany . |
| 6060104 | 4/1985 | Japan . |

OTHER PUBLICATIONS

Japanese Patent Abstract—Pub. No. 01–077583 (JP 1077583 A), Kiyoyasu et al., filed Sep. 18, 1987.
Japanese Patent Abstract—Pub. No. 01–077584 (JP 1077584 A), Kiyoyasu et al., filed Sep. 18, 1987,
Chemical Abstracts, vol. 107, No. 24, Dec., 1987, 226012v.
Chemical Abstracts, vol. 66, No. 19, May, 1967, 85771n.
Chemical Abstracts, vol. 82, No. 8, Feb. 1975, 44610w.
Chemical Abstracts, No. 67, No. 14, Oct. 1967, 64842s.
Chemical Abstracts, No. 70, No. 23, Jun., 1969, 105898x.
*Encyclopedia of Polymer Science and Engineering*, vol. 11, edited by J. L. Kroschwitz, Wiley Interscience (New York: 1987) pp. 558–571.
Kosar, *Light Sensitive Systems*, J. Wiley and Sons (New York: 1965), pp. 361–369.
U. Von Gizycki, *Angew. Chem. Int. Ed. Eng.*, 1971, 10, 403.
Wakabayashi et al., *Bulletin of the Chemical Society of Japan*, 1969, 42, 2924.

*Primary Examiner*—Gary Geist
*Assistant Examiner*—Catherine Kilby Scalzo
*Attorney, Agent, or Firm*—Gary L. Griswold; Walter N. Kirn; David L. Weinstein

[57] ABSTRACT

Radiation-sensitive organo-halogen compounds having a photo-labile halomethyl-1,3,5-triazine moiety and at least one polymerizable moiety within one molecule is provided. The compounds of this invention have at least one halomethyl substituent attached to a carbon atom of the triazine moiety and at least one polymerizable monomeric moiety attached to another atom of the triazine moiety. The compounds of this invention can be used to prepare polymers having 1,3,5-triazine substituents attached thereto. The compounds of this invention are good photoinitiators, and compositions containing them can be used in printing, duplicating, copying, and other imaging systems. The compounds of this invention are capable of stimulation by actinic radiation at a wavelength of about 250 to 900 nanometers to generate free radicals.

15 Claims, No Drawings

HALOMETHYL-1,3,5-TRIAZINES CONTAINING A MONOMERIC MOIETY

This is a division of application Ser. No. 08/049,555 filed Apr. 19, 1993, now U.S. Pat. No. 5,387,682, which is a continuation of application Ser. No. 07/555,301, abandoned, filed Jul. 18, 1990, which is a continuation-in-part of application Ser. No. 07/241,691, filed Sep. 7, 1988, abandoned.

BACKGROUND OF THE INVENTION

1. Field of the Invention

The present invention relates to photosensitive compounds, more particularly, derivatives of halomethyl-1,3,5-triazines.

2. Discussion of the Prior Art

Compounds that decompose to generate free radicals (free radical generating agents) upon exposure to light are well known in the graphic arts. Organic halogen compounds, which are capable of generating free radicals such as a chlorine free radical or a bromine free radical upon exposure to light, have been widely used as photoinitiators in photopolymerizable compositions, as photoactivators in free radical photographic compositions, and as photoinitiators for reactions catalyzed by acids formed by light. The spectral sensitivity of these compositions may be broadened by the addition of sensitizers, which, in essence, transfer their absorbed energy to the organic halogen compound. The use of such halogen compounds in photopolymerization processes and free radical photographic processes have been described in Kosar, *Light-Sensitive Systems*, J. Wiley & Sons (New York, 1965), pp. 180–181, 361–370.

Halomethyl-1,3,5-triazines are known to be initiators for a number of photochemical reactions. They are employed to produce free radicals for initiating polymerization or color changes and for initiating secondary reactions upon liberation of acid by the interaction of the free-radicals when hydrogen donors are present.

Examples of the use of halomethyl-1,3,5-triazines in the free radical polymerization of acrylate monomers are described in U.S. Pat. No. 3,905,815; U.S. Pat. No. 3,617,288; U.S. Pat. No. 4,181,752; U.S. Pat. No. 4,391,687; U.S. Pat. No. 4,476,215; and DE 3,517,440. U.S. Pat. No. 3,779,778 discloses the photoinitiated acid catalyzed decomposition of pyranyl ether derivatives to produce photosolubilizable compositions useful as positive printing plates. Chromophore substituted styryl-1,3,5-triazines and their uses are disclosed in U.S. Pat. No. 3,987,037 and U.S. Pat. No. 3,394,475.

Radiation sensitive compositions containing bi- and polyaromatic substituted triazines are disclosed in U.S. Pat. No. 4,189,323.

SUMMARY OF THE INVENTION

This invention provides radiation-sensitive organo-halogen compounds that have a photo-labile halomethyl-1,3,5-triazine moiety and a polymerizable monomeric moiety within one molecule. The compounds of this invention have at least one halomethyl substituent attached to a carbon atom of the triazine nucleus, preferably a trihalomethyl substituent, and at least one polymerizable monomeric moiety attached to another carbon atom of the triazine nucleus. The polymerizable monomeric moiety is polymerizable by ionic chain polymerization or by free radical polymerization. In certain situations, it can be polymerizable by active species released from the halomethyl-1,3,5-triazine moiety upon exposure of the compound to actinic radiation. The close proximity of the initiating moiety, i.e., the triazine, to the monomeric moiety increases the efficiency of photoinitiated polymerization of the compounds of this invention.

The compounds of this invention are good photoinitiators. Photopolymerizable and photocrosslinkable compositions containing them can be used in printing, duplicating, copying, and other imaging systems. The compounds of this invention are also useful in the preparation of polymers having halomethyl-1,3,5-triazine substituents attached thereto.

DETAILED DESCRIPTION OF THE INVENTION

As used herein, the term "monomeric moiety" means a moiety containing at least one group that is capable of undergoing free radical or ionic chain polymerization. Halomethyl substituted, 1,3,5-triazine compounds of this invention can be represented by the general formula I:

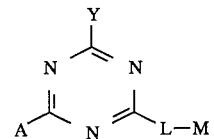

wherein

A represents a member selected from the group consisting of mono-, di- and trihalomethyl groups, Y represents a member selected from the group consisting of —A, —L—M, —NH$_2$, —NHR, —NR$_2$, —OR, and —R', where each R independently represents a member selected from the group consisting of substituted or unsubstituted alkyl groups, and substituted or unsubstituted aryl groups, and R' represents a member selected from the group consisting of substituted or unsubstituted alkyl groups, substituted or unsubstituted aryl groups, substituted or unsubstituted alkenyl groups, substituted or unsubstituted polyalkenyl groups, substituted or unsubstituted alkynyl groups, substituted or unsubstituted polyalkynyl groups, and substituted or unsubstituted heteroaromatic groups, M represents a group containing at least one monomeric moiety that is capable of undergoing free radical or ionic chain polymerization, and L represents a group or a covalent bond linking the monomeric moiety to the triazine nucleus.

Halomethyl groups that are suitable for A in the present invention include chloro-, bromo-, and iodomethyl groups, with chloro- and bromomethyl groups being preferred. Trihalomethyl groups are preferred; most preferred are trichloromethyl, tribromomethyl, and triiodomethyl groups.

Y represents any of a variety of substituents that are useful in modifying the physical, e.g., solubility, or chemical properties of the molecule, and preferably represents A, L—M, or R'. When Y represents A, the maximum number of halomethyl groups per triazine nucleus can be made available for free radical generation. When Y represents L—M, the chemical composition for both L—M groups can be the same, or it can be different, depending on the composition of linking group L, monomeric group M, or both When Y represents R', and in particular when R' represents an aryl, aralkenyl, aralkynyl, or heterocyclic aromatic group, the spectral sensitivity of the molecule can be varied, based on the photochemical response of R' to actinic radiation.

When R or R' represents an alkyl group, it is preferred that it have one to twelve carbon atoms, more preferably one to six carbon atoms.

When R or R' represents an aryl group, it is preferred that the group have no more than five fused rings, more preferably no more than three fused rings, such as, for example, phenyl, naphthyl, anthracenyl.

When R represents a substituted aryl group, suitable substituents include, but are not limited to, halogen atoms; alkyl groups, preferably having one to twelve carbon atoms; aryl groups; alkoxy groups; aryloxy groups; alkylthio groups; amino groups, carboxylic acid groups and their esters; acyl groups; acyl amino groups; nitro groups; and sulfonic acid groups.

When R' represents a substituted aryl group, substituents can include not only the substituents that are suitable for R when R represents an aryl group, but also a substituted alkenyl or polyalkenyl group, preferably having one to six conjugated carbon-to-carbon double bonds, more preferably one to two conjugated carbon-to-carbon double bonds, and substituted with an aryl or heteroaromatic group (such as phenyl, 4-methoxy-1-naphthyl, 2-benzothiazole); a substituted alkynyl group, preferably having one to three conjugated carbon-to-carbon triple bonds, more preferably one ethynyl group, and substituted with an aryl or heteroaromatic group (such as phenyl, 2-thienyl).

When R' represents a heteroaromatic group, it is preferred that the group contain a maximum of three fused rings. It is preferred that the heteroatoms be selected from the group consisting of nitrogen, oxygen, sulfur, and combinations thereof. Examples of heteroaromatic groups useful as R' include, but are not limited to, those derived from a furan group, a thiophene group, a pyrrole group, a pyridine group, an oxazole group, an isooxazole group, a thiazole group, an imidazole group, a benzofuran group, a benzothiophene group, a benzimidazole group, a benzotriazole group, a quinoline group, a benzoxazole group, and a benzothiazole group. Other examples of heteroaromatic groups that can be substituted on halomethyl-1,3,5-triazines are recited in U.S. Pat. No. 3,987,037 and U.S. Pat. No. 4,772,534. Whenever R' represents a substituted heteroaromatic group, the substituents can be selected from those that can be used as substituents for R when R represents a substituted aryl group.

When R' represents an alkenyl or polyalkenyl group, it is preferred that the group have one to six conjugated carbon-to-carbon double bonds, more preferably one to three conjugated carbon-to-carbon double bonds, and substituted with an aryl or heteroaromatic group (such as phenyl, 2-benzoxazole). It is preferred that the alkenyl group have two to six carbon atoms.

When R' represents an alkynyl or polyalknyl group, it is preferred that the group have one to three conjugated carbon-to-carbon triple bonds, more preferably one ethynyl group, and substituted with an aryl or heteroaromatic group (such as phenyl, 2-pyridyl).

When R' is substituted with a heteroaromatic group, these heteroaromatic groups can be the same as those previously described herein.

When R or R' represents an alkyl group, aryl group, or heteroaromatic group, the particular identity of R and R' and their substituents, if any, is not critical. Certain groups may be selected to impart or modify a physical property of the compounds of this invention, such as solubility, softness, or hardness. Alternatively, R, R', and substituents can be selected to impart a certain spectral response to the triazine moiety within the compounds of this invention, based on their intended use.

When R or R' represents a substituted group, the particular identity of R, R', and their substituents is not critical. However, they should be selected so as not to adversely affect the polymerizability or the photoinitiation capability of the compounds of this invention. For example, a few chemical substances can suppress free radical polymerization by reacting with the initiating and propagating radicals. Groups that essentially completely halt polymerization until they are consumed are referred to as inhibitors. Groups that suppress polymerization less effectively than inhibitors are referred to as retarders. A discussion of inhibition and retardation can be found in G. Odian, *Principles of Polymerization*, J. Wiley & Sons (New York: 1981). Some examples of common inhibitor and retarder moieties include quinones, such as benzoquinone, chloranil; hydroquinones and their alkyl ethers, such as hydroquinone, t-butylcatechol, p-hydroxyanisole; and hindered phenols such as 2,6-di-t-butylphenol; aromatic nitro groups such as nitrobenzene, 1,3,5-trinitrobenzene, 2,2-diphenyl-1-picrylhydrazil. One method of determining whether a particular species of R, R', or a substituent thereof adversely affects the polymerization capability of a compound of this invention is to dissolve the compound in a liquid polyfunctional monomer such as trimethylolpropane triacrylate or trimethacrylate, pentaerythitol triacrylate or tetraacrylate, neopentyl glycol diacrylate, ethylene glycol diacrylate, or hexanediol diacrylate at a level of 1 to 5% by weight. To aid in dissolution, it may be necessary to warm the mixture or it may be necessary to predissolve the compound in a volatile organic solvent such as dichloromethane, ethyl acetate, diethyl ether, toluene, or methanol prior to addition to the monomer. The solvent can be evaporated by warming the solution containing the compound being tested. The solution is then either coated on a substrate, such as polyester film, or poured into a shallow vessel, such as a weighing dish. An additional film which is transparent to the actinic radiation can optionally be placed on the surface of the sample to minimize the effect of oxygen. The sample is then exposed for one to five minutes to actinic radiation, i.e., light of sufficient intensity and wavelength, that would be expected to stimulate decomposition of the 1,3,5-halomethyltriazine as a photoinitiator. Examples of commonly available light sources are the five kw Berkey Ascor 30×40 in. vacuum unit (Berkey Corporation) or the Linde Photocure System Unit (Union Carbide Corporation) equipped with a nitrogen atmosphere. The solution containing the compound being tested will remain unchanged whenever a R, R', or a substituent thereof is present that will adversely affect polymerization. Compounds within the scope of this invention will result in polymerization of the solution containing the compound being tested to produce a noticeable change in viscosity and/or in many instances to actually form a solid mass. Sometimes, the surface of the solution exposed to air will remain fluid whenever oxygen is present due to oxygen inhibition. However, the bulk of the solution will polymerize.

Monomeric moieties designated by M can be selected from monomeric groups capable of free-radical or ionic chain polymerization. Preferably, monomeric moieties are selected from the group consisting of acrylates, methacrylates, acrylamides, vinyl ethers, allyl ethers, epoxides, and allyl amines. Most preferred are the acrylates, methacrylates, acrylamides, and vinyl ethers. There is no upper limit on the number of monomeric moieties per triazine nucleus; however, there must be at least one monomeric moiety per triazine nucleus. Preferably, there are one to twelve monomeric moieties per triazine nucleus; more preferably, there are one to six monomeric moieties per triazine nucleus. If more than one monomeric moiety is present per triazine nucleus, they can be from different generic classes or can be different species from the same generic class.

L represents a group that links the monomeric moiety or moieties to the triazine nucleus. The precise identity of L is not critical, but it should be selected so that it does not interfere with or adversely affect the polymerizability or photoinitiation capability of the compound as discussed previously. The method described for determining whether a particular linking group L adversely affects polymerization capability is the same as that described previously for R, R', and substituents thereof. L can be formed from a single group or it can be formed from a combination of groups. In addition, L also includes a covalent bond. Groups that are suitable for linking groups include carbamato (—NHCO$_2$—), urea (—NHCONH—), amino (—NH—), amido (—CONH—), aliphatic, e.g., having up to 10 carbon atoms, alkyl, e.g., having up to 10 carbon atoms, haloalkyl, e.g., having up to 10 carbon atoms, alkenyl, e.g., having up to 10 carbon atoms, alkynyl, e.g., having up to 10 carbon atoms, aryl, e.g., having up to three rings, heteroaryl, e.g., having up to three rings, styryl, ester (—CO$_2$—), ether (—O—), and combinations thereof. Based on ease of synthesis, the most preferred groups for attachment directly to the triazine nucleus are carbamato, urea, amino, alkenyl, aryl, and ether.

The following list exemplifies typical —L—M group combinations:

—NHCO$_2$CH$_2$CH$_2$OCOCH=CH$_2$
—NHCO$_2$CH$_2$CH$_2$OCOC(CH$_3$)=CH$_2$
—NHCO$_2$CH$_2$CH=CH$_2$
—NHCONHCH$_2$CH=CH$_2$
—NHCH$_2$CH$_2$OCONHCH$_2$CH$_2$OCOCH=CH$_2$
—N(CH$_2$CH$_2$OCONHCH$_2$CH$_2$OCOCH=CH$_2$)$_2$
—N(CH$_2$CH$_2$OCOCH=CH$_2$)$_2$
—OCH$_2$CH=CH$_2$
—N(CH$_2$CH=CH$_2$)$_2$
—C$_6$H$_4$—p—OCOCH=CH$_2$
—C$_6$H$_4$—p—OCH$_2$CH$_2$OCOCH=CH$_2$
—CH=CH—C$_6$H$_4$—p—OCH$_2$CH$_2$OCOCH=CH$_2$
—CH=CH—C$_6$H$_4$—p—O—CH$_2$CH$_2$OCOC(CH$_3$)$_2$NHCOCH(CH$_3$)=CH$_2$
—NHCO$_2$CH$_2$CH$_2$CH$_2$OCH=CH$_2$

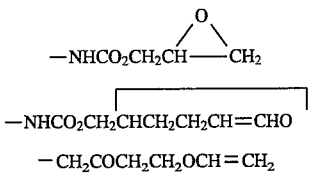

—NHCO$_2$CH$_2$CHCH$_2$CH$_2$CH=CHO

—CH$_2$COCH$_2$CH$_2$OCH=CH$_2$

Representative examples of preferred compounds of this invention have the structures shown in Table I.

TABLE I

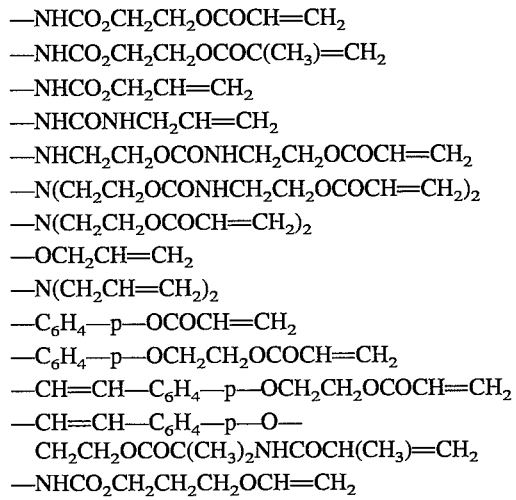

| | A | L-M |
|---|---|---|
| 1 | —CCl$_3$ | —NHCOCH$_2$CH$_2$OCCH=CH$_2$ |
| 2 | —CCl$_3$ | —NHCOCH$_2$CH$_2$OCC(CH$_3$)=CH$_2$ |
| 3 | —NHCOCH$_2$CH$_2$OCCH=CH$_2$ | —NHCOCH$_2$CH$_2$OCCH=CH$_2$ |
| 4 | —NHCOCH$_2$CH$_2$OCC(CH$_3$)=CH$_2$ | —NHCOCH$_2$CH$_2$OCC(CH$_3$)=CH$_2$ |
| 5 | —CCl$_3$ | —NHCOCH$_2$CH$_2$CH$_2$OCC(CH$_3$)=CH$_2$ |
| 6 | —CCl$_3$ | —OCH$_2$CH=CH$_2$ |
| 7 | —CCl$_3$ | —NHCNHCH$_2$CH=CH$_2$ |
| 8 | —CCl$_3$ | —NHCN(CH$_2$CH=CH$_2$)$_2$ |
| 9 | —CCl$_3$ | —NHCH$_2$CH=CH$_2$ |
| 10 | —CCl$_3$ | —N(CH$_2$CH=CH$_2$)$_2$ |

TABLE I-continued

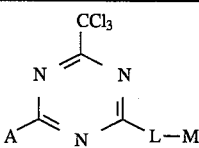

| | A | L–M |
|---|---|---|
| 11 | 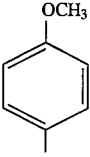 4-methoxyphenyl | 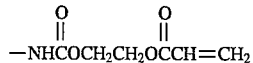  —NHCOCH$_2$CH$_2$OCCH=CH$_2$ (with two C=O) |
| 12 | 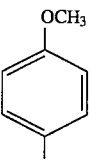 4-methoxyphenyl | —NHCOCH$_2$CH$_2$OCC(CH$_3$)=CH$_2$ |
| 13 | 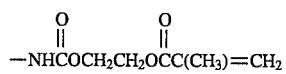 3,4-dimethoxyphenyl | —NHCOCH$_2$CH$_2$OCCH=CH$_2$ |
| 14 | 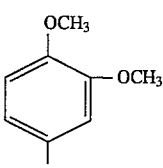 3,4-dimethoxyphenyl | —NHCOCH$_2$CH$_2$OCC(CH$_3$)=CH$_2$ |
| 15 | 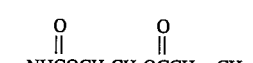 9-anthryl-CH=CH— | —NHCOCH$_2$CH$_2$OCCH=CH$_2$ |
| 16 | —CCl$_3$ | 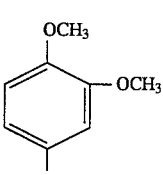 naphthyl-OCH$_2$CH$_2$OCC(CH$_3$)=CH$_2$ |
| 17 | —CCl$_3$ |  phenyl-N[CH$_2$COCH$_2$CH$_2$OCC(CH$_3$)=CH$_2$]$_2$ |
| 18 | —CCl$_3$ | 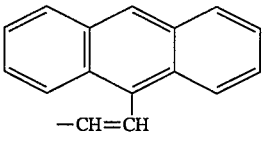 phenyl-COCH$_2$CH$_2$OCCH=CH$_2$ |
| 19 | —CCl$_3$ | —CH=CH——OCH$_2$CH$_2$OCC(CH$_3$)=CH$_2$ |

TABLE I-continued

| | A | L–M |
|---|---|---|
| 20 | $-CCl_3$ | $-CH=CH-C_6H_4-OCH_2CH_2OCC(CH_3)_2-NH-C(=O)-C(CH_3)=CH_2$ |
| 21 | $-NHCOCH_2CH_2OCC(CH_3)=CH_2$ | $-C_6H_4-CH=CH-C_6H_4-OCH_2CH_2OCC(CH_3)_2NHCCH=CH_2$ |
| 22 | $-C(CH_3)=CH-C(CH_3)=CH-C_6H_5$ | $-NHCOCH_2CH_2OCCH=CH_2$ |
| 23 | $-C_6H_4-C\equiv C-C_6H_4-OCH_3$ | $-NHCOCH_2CH_2OCC(CH_3)=CH_2$ |
| 24 | 2-thienyl | $N[CH_2CH_2OCC(CH_3)=CH_2]_2$ |
| 25 | $-CCl_3$ | $-CH=CH-CH$ (benzoxazoline with $CH_2CH_2OCCH=CH_2$ on N) |
| 26 | $-CCl_3$ | $-CH=CH-$(furan)$-CH_2OCC(CH_3)=CH_2$ |
| 27 | $N[CH_2CH_2OCNHCH_2CH_2OCC(CH_3)=CH_2]_2$ | $C_6H_4-C(=O)-C=$(benzothiazoline with $CH_2CH_2OCNHCH_2CH_2OCC(CH_3)=CH_2$ on N) |
| 28 | $-CH=CH-$(1-methyl-2-(4-methoxyphenyl)indol-3-yl) | $-NHCOCH_2NHCCH=CH_2$ |
| 29 | $-CCl_3$ | $-NHCOCH_2CH_2CH_2OCH=CH_2$ |

TABLE I-continued

Structure:
```
         CCl3
          |
          C
         / \
        N   N
        ||   ||
        C   C
       / \ / \
      A   N   L—M
```

| | A | L-M |
|---|---|---|
| 30 | 4-methoxyphenyl (OCH₃ at para position) | $-NHCOCH_2CH_2CH_2CH_2OCH=CH_2$ |
| 32 | $-NHCOCH_2C(CH_2OCCH=CH_2)_3$ (with two C=O groups) | $-NHCOCH_2C(CH_2OCCH=CH_2)_3$ (with two C=O groups) |

From the foregoing table, it should not be inferred that the halomethyl groups suitable for the compounds of this invention are to be limited to —$CCl_3$.

One method of preparing the compounds of this invention is by the addition reaction of isocyanato-substituted halomethyl-1,3,5-triazines with monomeric moiety sources having groups reactive with the isocyanate group. The isocyanato substituted triazines may be prepared from the corresponding amino derivative according to the procedure of U. Von Gizycki, Agnew. Chem. Int. Ed. Eng., 1971, 10, 403. Isocyanato-1,3,5-triazines suitable for this reaction include:

2,4-bis(trichloromethyl)-6-isocyanato-1,3,5-triazine 2-isocyanato-4-methyl-6-trichloromethyl-1,3,5-triazine 2-isocyanato-4-phenyl-6-trichloromethyl-1,3,5-triazine 2-isocyanato-4-methoxy-6-trichloromethyl-1,3,5-triazine 2-isocyanato-4-(p-methoxyphenyl)-6-trichloromethyl-1,3,5-triazine 2-isocyanato-4-(p-methoxystyryl)-6-trichloromethyl-1,3,5-triazine 2-isocyanato-4-(m,p-dimethoxyphenyl)-6-trichloromethyl-1,3,5-triazine Suitable reagents that contain monomeric moieties and that will combine with the isocyanato group include 2-hydroxyethyl acrylate, 2-hydroxyethyl methacrylate, allyl alcohol, diallyl amines, 2-hydroxyethyl acrylamide, and hydroxybutyl vinyl ether.

The isocyanate addition reaction can be carried out in the presence of solvents, such as, for example, toluene, pyridine, benzene, xylene, dioxane, tetrahydrofuran, etc., and mixtures of solvents. The duration and temperature of the reaction is dependent on the particular compounds and the catalyst employed. Generally, temperatures of about 25° to 150° C. for from one to seventy-two hours are sufficient to provide for the reaction. Preferably, the reaction is carried out at room temperature from three to seventy-two hours. The preferred catalyst is di-n-butyltin dilaurate.

Another method for preparing the compounds of this invention involves attaching the monomeric moiety to a group pendant from the triazine nucleus, such as a hydroxyl or amino group. Reagents that are useful in such a method include acryloyl or methacryloyl chloride, 2-isocyanatoethyl methacrylate, and vinyl oxazolinones. The reaction with acryloyl or methacryloyl chloride can be carried out in the presence of solvents, such as, for example, benzene, pyridine, toluene, xylene, etc., and mixtures of solvents. The duration and temperature of the reaction is dependent on the particular compounds and the catalyst for the reaction. Generally, temperatures of about 25° to 150° C. for from one to seventy-two hours are sufficient. Preferably, the reaction is carried out at 80°–110° C. for from three to seventy-two hours. The preferred catalyst is 4-N,N-dimethylaminopyridine. The vinyl oxazolinone reaction is reviewed in *Encyclopedia of Polymer Science and Engineering*, Vol. 11, edited by J. I. Kroschwitz, Wiley Interscience (New York: 1987), p. 558.

Suitable hydroxyl or amino substituted halomethyl-1,3,5-triazines which can be modified by this method include:

2-amino-4,6-bis(trichloromethyl)-1,3,5-triazine 2-(2-hydroxyethylamino)-4,6-bis(trichloromethyl)-1,3,5-triazine 2-[bis(2-hydroxyethyl)amino]-4,6-bis(trichloromethyl)-1,3,5-triazine 2,4-bis(2-hydroxyethylamino)-6-trichloromethyl-1,3,5-triazine 2,4-bis[bis(2-hydroxyethyl)ethylamino]-6-trichloromethyl-1,3,5-triazine 2-(2-hydroxyethylamino)-4-methoxy-6-trichloromethyl-1,3,5-triazine 2,4-bis(trichloromethyl)-6-(p-hydroxyphenyl)-1,3,5-triazine 2,4-bis(trichloromethyl)-6-(p-hydroxystyryl)-1,3,5-triazine 2,4-bis(trichloromethyl)-6-[p-(2-hydroxyethoxy)phenyl]-1,3,5-triazine 2,4-bis(trichloromethyl)-6-[p-(2-hydroxyethoxy-)styryl]-1,3,5-triazine Another method of preparing the compounds of this invention is the cotrimerization of organic nitriles having a monomeric substituent with haloacetonitriles in accordance with the teachings of Wakabayashi et al, Bulletin of the Chemical Society of Japan, 1969, 42, 2924. Still another method is the condensation reaction of an aldehyde compound having a monomeric functionality in accordance with the teachings of U.S. Pat. No. 3,987,037. Another method is the nucleophilic displacement reaction of the halomethyl group of a 1,3,5-triazine using monomers having free hydroxy or amino groups.

The monomer-containing halomethyl-1,3,5-triazines of this invention are particularly useful in photopolymerizable compositions containing ethylenically unsaturated monomeric compounds. A discussion of the free radical polymerization process can be found in Chapter 1 of *UV-curing: Science and Technology,* Vol. II, edited by S. P. Pappas, Technology Marketing Corporation, Norwalk, Conn. (1985). The initiation step is generally believed to first involve the light induced decomposition of the halocarbon initiator to generate a radical species (e.g., R·) which will add to the double bond of the group containing the monomeric moiety (i.e., M) to form a species (R—M·) necessary for starting the next step of chain propagation. A key factor influencing the efficiency or rate at which the chain propagating species is formed will depend on the ease at which the two species R· and M can combine. The photoinitiators of the invention are expected to perform efficiently in this regard because of the close proximity of each unit, i.e., being within a molecular dimension of one another, in contrast to the situation of requiring the photogenerated radical species R· to diffuse through the composition matrix to a more distant monomer molecule. In actual practice, one must consider other factors in determining to what extent this improvement influences the overall efficiency of a particular photopolymerizable composition. These other factors include initiator concentration, monomer concentration, monomer reactivity, type of binder additives, the degree of inhibition reactions influencing polymer formation by various possible termination steps, and the nature of the final desired effect (e.g., insolubility, hardness, degree of tack, adhesion and others).

The compounds of this invention are also useful as monomeric reagents for the preparation of polymers, copolymers, and composites having halomethyl-1,3,5-triazine substituents. Polymers containing halomethyl-1,3,5triazine moieties are useful as photoinitiators and as photocrosslinkable materials. The polymerization reactions may be carried out using the procedures described in G. Odian, *Principles of Polymerization,* J. Wiley & Sons (New York: 1981) for radical chain or ionic chain polymerization, depending on the specific monomeric substituent. Of particular importance are the compounds of this invention that have one acrylate, methacrylate, or acrylamide substituent. These compounds may be homopolymerized or copolymerized with various other vinyl monomers such as styrene, halogenated olefins, vinyl esters, acrylates, methacrylates, acrylic acid, methacrylic acid, acrylonitrile, and acrylamides. Polymeric materials can be designed to have a wide range of structural and physical properties such as solubility, compatibility, molecular weight, light absorption, etc.

The sensitivity of compositions containing the compounds of this invention to actinic radiation of a particular range of wavelengths can be increased by the incorporation of known ultraviolet and visible light sensitizers including cyanine, carbocyanine, merocyanine, styryl, acridine, polycyclic aromatic hydrocarbons, polyarylamines, and amino-substituted chalcones. Suitable cyanine dyes are described in U.S. Pat. No. 3,495,987. Suitable styryl dyes and polyarylamines are described in Kosar, *Light Sensitive Systems,* J. Wiley and Sons (New York, 1965), pages 361–369. Polycyclic aromatic hydrocarbons useful as sensitizers, an example of which is 2-ethyl-9,10-dimethoxyanthracene, are disclosed in U.S. Pat. No. 3,640,718. Amino substituted chalcones useful as sensitizers are described in U.S. Pat. No. 3,617,288. The compounds of this invention can be used in photosensitive compositions in combination with other photoinitiators including benzophenones, benzoin ethers, thioxanthone, benzil, and Michler's ketone. The compounds of this invention can also be substituted for the triazines used in conjunction with dialkylamino aromatic carbonyl compounds disclosed in U.S. Pat. No. 4,259,432; 2-(benzoylmethylene)-5-benzothiazolidene thiazole-4-1 compounds disclosed in E application 0109291, May 23, 1984; 3-keto-substituted coumarin compounds disclosed in U.S. Pat. No. 4,505,793; U.S. Pat. No. 4,239,850; Jpn. Kokai Tokkyo Koho JP 60 60,104 (85 60104); and Ger. Offen. 2,851,641.

Photopolymerizable compositions wherein the compounds of this invention can be used as photoinitiators typically comprise an unsaturated, free radical initiated, chain propagating addition polymerizable compound, a compound of this invention, and optionally one or more fillers, binders, dyes, polymerization inhibitors, color precursors, oxygen scavengers, etc. The compound of this invention should be present in an amount sufficient to initiate polymerization of the polymerizable compound. Examples of suitable ratios of ingredients are as follows: for every 100 parts of polymerizable compound there can be present from 0.005 to 10 parts of photoinitiator, from 0 to 200 parts of filler, from 0 to 200 parts of binder, and from 0 to 10 or more parts of dyes, polymerization inhibitors, color precursors, oxygen scavengers, etc., as may be needed for a particular use of the photopolymerizable compositions. Preferably, there is used per 100 parts of polymerizable compounds 1 to 7.5 parts of the compound of this invention and from 25° to 150 parts of binder.

Unsaturated, free-radical initiated, chain-propagating addition polymerizable compounds suitable for use with the compound of this invention include alkylene or polyalkylene glycol diacrylates, e.g., ethylene glycol diacrylate, diethylene glycol diacrylate, glycerol diacrylate, glycerol triacrylate, ethylene glycol dimethacrylate, 1,3-propanediol dimethacrylate, 1,2,4-butanetriol trimethacrylate, 1,4-cyclohexanediol diacrylate, pentaerythritol tetramethacrylate, pentaerythritol triacrylate, sorbitol hexacrylate; bis[1-(3-acryloxy-2-hydroxy)]-p-propoxyphenyl dimethylmethane, bis[1-(2-acryloxy)]-p-ethoxyphenyl-dimethylmethane, tris hydroxyethyl-isocyanurate trimethacrylate, the bis-acrylate and the bis-methacrylates of polyethylene glycols of molecular weight 200–500 and the like; unsaturated amides, e.g., methylene bis-acrylamide, methylene bis-methacrylamide, 1,6-hexamethylene bis-acrylamide, diethylene triamine trisacrylamide, beta-methacrylaminoethyl methacrylate; vinyl esters such as divinyl succinate, divinyl adipate, divinyl phthalate. The preferred unsaturated compounds include pentaerythritol tetracrylate, bis[p-(3-acryloxy-2-hydroxypropoxy)phenyl]-dimethylmethane, and bis[p-(2-acryloxyethoxy)phenyl]-dimethylmethane. Mixtures of these esters can also be used as can mixtures of these esters with alkyl esters of acrylic acid and methacrylic acid, including such esters as methyl acrylate, methyl methacrylate, ethyl acrylate, isopropyl methacrylate, n-hexyl acrylate, stearyl acrylate, allyl acrylate, diallyl phthalate, and the like.

To prepare the photosensitive compositions, the components can be admixed in any order and stirred or milled to form a solution or uniform dispersion. Photosensitive elements can be made by coating a photosensitive composition on a suitable base or support and drying the coating. The dry thickness typically ranges from about 0.00005 to about 0.075 inch.

Suitable bases or supports for the photosensitive compositions include metals, e.g., steel and aluminum plates, sheets and foils, and films or plates composed of various film-forming synthetic or high polymers, including addition polymers, e.g., vinylidene chloride, vinyl chloride, vinyl acetate, styrene, isobutylene polymers and copolymers; linear condensation polymers, e.g., polyethylene terephthalate, polyhexamethylene adipate, polyhexamethylene adipamide/adipate.

The invention will be more specifically illustrated by the following examples. All values of λmax were measured in methanol, unless otherwise indicated.

EXAMPLES 1–6

These examples illustrate the preparation of acrylate-containing and methacrylate-containing halomethyl-substituted- 1,3,5-triazine compounds by means of an isocyanate addition reaction.

Example 1

To a solution comprising 0.008 mol of 2-hydroxyethyl acrylate monomer, 12 drops di-n-butyltin dilaurate, and 100 mg phenothiazine in 30 ml dry toluene (freshly distilled from sodium in the presence of benzophenone) was added a toluene solution containing 0.006 mol 2,4-bis(trichloromethyl)-6-isocyanato-1,3,5-triazine. The reaction mixture was stirred at room temperature under nitrogen atmosphere for 24–72 hours. The solvent was removed at room temperature by means of a rotary evaporator under reduced pressure. The clear residue was dissolved in a small amount of dichloromethane and loaded upon a silica gel column (100 g packed in (1:1) dichloromethane/hexane) and eluted with dichloromethane. The major product was collected; the appropriate fractions were pooled; and the solvent was removed at room temperature by means of a rotary evaporator to yield the product. The product had a melting point of 115°–117° C. and λmax of 235 nm. The structural formula of the product is as follows:

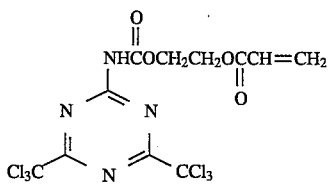

Example 2

The procedure of Example 1 was repeated with the exception being that 2-hydroxyethyl methacrylate was used instead of 2-hydroxyethyl acrylate. The product had a melting point of 66°–69° C. and λmax of 235 nm. The structural formula of the product is as follows:

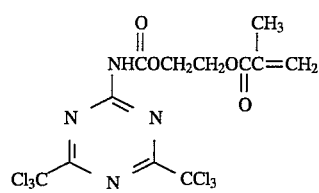

Example 3

The procedure of Example 1 was repeated with the exception being that 2,4-bis(isocyanato)-6-trichloromethyl-1,3,5-triazine was used instead of 2,4-bis(trichloromethyl)-6-isocyanato-1,3,5-triazine. The product was a gum and had a λmax of 219 nm. The structural formula of the product is as follows:

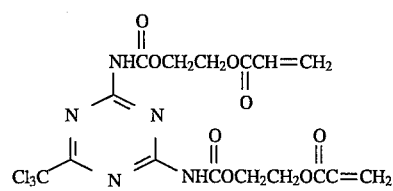

Example 4

The procedure of Example 2 was repeated with the exception being that 2,4-bis(isocyanato)-6-trichloromethyl-1,3,5-triazine was used instead of 2,4-bis(trichloromethyl)-6-isocyanato-1,3,5-triazine. The product was a gum and had a λmax of 220 nm. The structural formula of the product is as follows:

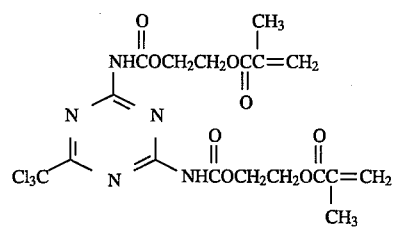

Example 5

The procedure of Example 1 was repeated with the exception being that 2-hydroxypropyl methacrylate was used instead of 2-hydroxyethyl acrylate. The product was a gum and had a λmax of 235 nm (measured in tetrahydrofuran). The structural formula of the product is as follows:

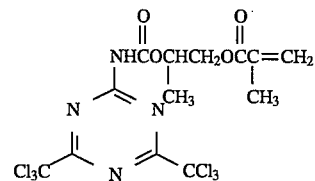

Example 6

The procedure of Example 1 was repeated with the exception being that bis[1-(3-acryloxy-2-hydroxy)] -p-propoxy-phenyl dimethylmethane was used instead of 2-hydroxyethyl acrylate. The product was a gum and had a λmax of 235 nm. The structural formula of the product is as follows:

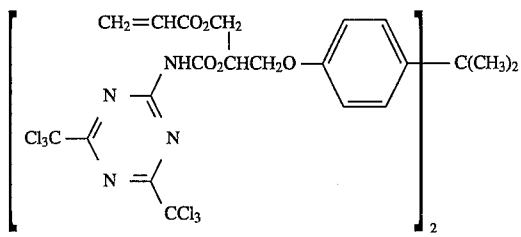

EXAMPLES 7–9

These examples illustrate the preparation of trichloromethyl-1,3,5-triazine compounds containing having an allyl group by means of an isocyanate addition reaction.

Example 7

Using the same procedure as was used in Example 1, 2-isocyanato-4,6-bis(trichloromethyl)-1,3,5-triazine was reacted with allyl alcohol. The product had a melting point of 79°–81° C. and a λmax of 236 nm (measured in tetrahydrofuran). The structural formula of the product is as follows:

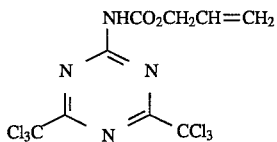

Example 8

Using the same procedure as was used in Example 1, 2-isocyanato-4,6-bis(trichloromethyl)-1,3,5-triazine was reacted with allyl amine. The product had a melting point of 170°–172° C. and a λmax of 229 nm (measured in tetrahydrofuran). The structural formula of the product is as follows:

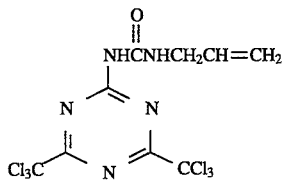

Example 9

Using the same procedure as was used in Example 1, 2-isocyanato-4,6-bis(trichloromethyl)-1,3,5-triazine was reacted with diallyl amine. The product had a melting point of 95°–98° C. and a λmax of 246 nm (measured in tetrahydrofuran). The structural formula of the product is as follows:

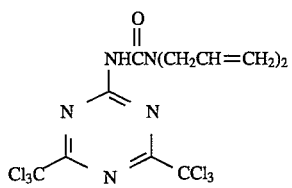

EXAMPLES 10–11

These examples illustrate the preparation of trichloromethyl-1,3,5-triazine compounds containing an allyl group by means of an amine nucleophilic displacement of a trichloromethyl group.

Example 10

To a solution comprising 2.3 mmol 2,4,6-tris(trichloromethyl)-1,3,5-triazine in 25 ml toluene was added 1 equivalent allyl amine. The reaction mixture was stirred at room temperature for 24 hours under a nitrogen atmosphere. The solvent was removed by means of a rotary evaporator under reduced pressure, and the residue was dissolved in a small amount of dichloromethane, loaded upon a column of silica gel (100 g packed in hexane), and eluted with hexane. The appropriate fractions were pooled and the solvent was removed by means of a rotary evaporator to afford product. The product was a gum having a λmax of 246 nm. The structural formula of the product is as follows:

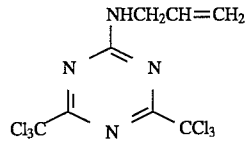

Example 11

The procedure of Example 10 was repeated, with the exception being that diallyl amine was used instead of allyl amine. The product had a melting point of 79°–81° C. and a λmax of 250 nm (measured in tetrahydrofuran). The structural formula of the product is as follows:

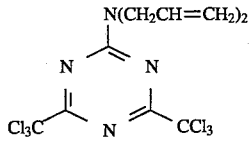

EXAMPLES 12–14

These examples illustrate the preparation of an acrylate, a methacrylate, and a vinyl ether derivative of a trichloromethyl-1,3,5-triazine compound by means of an isocyanate addition reaction.

Example 12

To a solution comprising 0.008 mol of a 2-hydroxyethyl acrylate monomer, 12 drops di-n-butyltin dilaurate, and 100 mg phenothiazine in 30 ml dry benzene (freshly distilled from sodium in the presence of benzophenone) was added a toluene solution containing 0.006 mol 2-isocyanato-4-(p-methoxyphenyl)-6-trichloromethyl-1,3,5-triazine. The reaction mixture was stirred at room temperature under a nitrogen atmosphere for 24–72 hours. The solvent was removed at room temperature by means of a rotary evaporator under reduced pressure. The clear residue was dissolved in a small amount of dichloromethane, loaded upon a silica gel column (100 g packed in (1:1) dichloromethane/hexane), and eluted with dichloromethane.

The major product was collected; the appropriate fractions were pooled; and the solvent was removed at room temperature by means of a rotary evaporator to yield the product. The product had a melting point of 116°–119° C. and a λmax of 310 nm (measured in methylene chloride). The structural formula of the product is as follows:

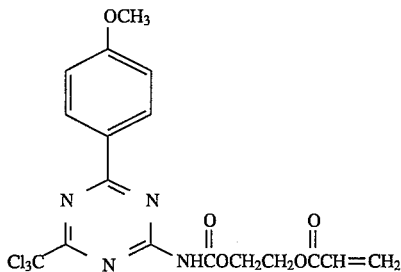

Example 13

The procedure of Example 12 was repeated, with the exception being that 2-hydroxyethyl methacrylate was used instead of 2-hydroxyethyl acrylate. The product had a melting point of 131°–133° C. and a λmax of 308 nm (measured in methylene chloride). The structural formula of the product is as follows:

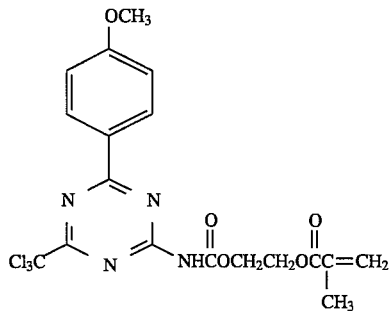

Example 14

The procedure of Example 1 was repeated, with the exception being that 4-hydroxybutylvinylether was used instead of 2-hydroxyethyl acrylate. The product had a melting point of 218°–222° C. and a λmax of 285 nm (measured in methylene chloride). The structural formula of the product is as follows:

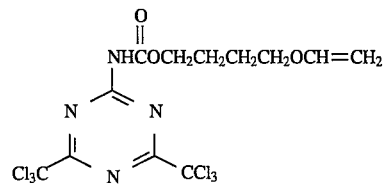

Example 15

This example illustrates the preparation of a methacrylate derivative of a halomethyl substituted-1,3,5-triazine compound by means of the reaction of a hydroxy substituted trichloromethyl-1,3,5-triazine and 2-isocyanatoethyl methacrylate. To a slurry of 1.50 gms of 2,4-bis(trichloromethyl)-6-[p-(2-hydroxyethoxy)styryl]-1,3,5-triazine in 50 ml of toluene/methylene chloride (4:1) was added 0.65 g isocyanatoethyl methacrylate and three drops di-n-butyltin dilaurate. The reaction was stirred at room temperature overnight and the solvent was removed under reduced pressure by means of a rotary evaporator. The yellow solid was recrystallized with ethanol to yield 1.8 g of the desired product. The product had a melting point of 130°–132° C. and a λmax of 374 nm. The structural formula of the product is as follows:

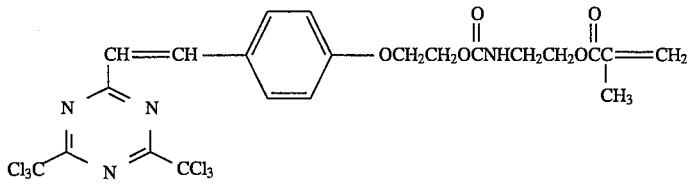

Example 16

This example illustrates the preparation of a methacrylate derivative of a halomethyl substituted-1,3,5-triazine compound by means of the reaction of a hydroxy substituted trichloromethyl-1,3,5-triazine and methacryloyl chloride. To a solution of 1.55 g of 2,4-bis(trichloromethyl)-6-[p-(2-hydroxyethoxy)styryl]-1,3,5-triazine in 50 ml of methylene chloride was added 0.6 g of methacryloyl chloride and 0.6 g of triethyl amine. Upon standing at room temperature for 24 hours, a white solid that had formed, was filtered, and discarded. An additional 50 ml of methylene chloride was added to the filtrate which was then washed twice with solutions of 2N HCl and saturated NaHCO₃. After drying with MgSO₄, the solvent was removed to give 0.8 g of a yellow oil, which solidified upon trituration with hexane/ethanol and cooling. Recrystallization with absolute ethanol gave mainly the methacrylate ester of the starting triazine with minor impurities. The product had a melting point of 110°–118° C. and a λmax of 372 nm (measured in ethyl acetate). The structural formula of the product is as follows:

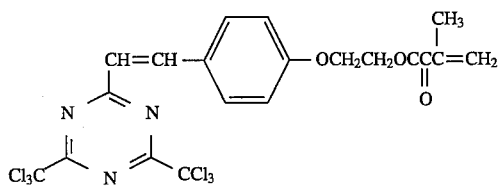
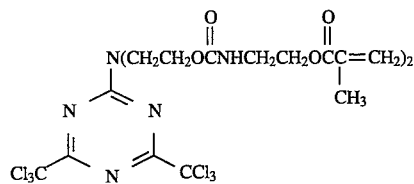

Example 17

This example illustrates the preparation of an acrylamide derivative of a trichloromethyl-1,3,5-triazine compound by means of the reaction of an isopropenyloxazolin-5-one. A solution containing 5.0 g of 2,4-bis(trichloromethyl)-6-[p-(2-hydroxyethoxy)-styryl]-1,3,5-triazine, 1.8 g of 2-isopropenyl-4,4-dimethyl-2-oxazolin-5-one, and 0.1 g of 1,8-diazabicyclo- 5.4.0]undec-7-ene in 50 ml of methylene chloride was refluxed for 12 hours and allowed to stand at room temperature for 48 hours. Some insoluble material had formed which was filtered. The methylene chloride was removed under reduced pressure to yield a yellow orange solid containing about 83% of the desired acrylamide product of Example 16 and about 11% of the starting triazine as determined by HPLC. Further purification by recrystallization with ethanol containing a small amount of methylene chloride gave purer product having a melting point of 176°–179° C. and a λmax of 337 nm (measured in methylene chloride). The structural formula of the product is as follows:

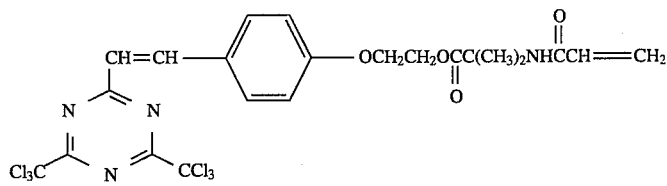

Example 18

This example illustrates the preparation of a dimethacrylate derivative of a trichloromethyl-1,3,5-triazine compound by means of the reaction of a diol and an isocyanatoethyl methacrylate. A solution containing 2.28 g of 2-bis(2-hydroxyethyl)amino-4,6-bis(trichloromethyl)- 1,3,5-triazine and 1.69 g of 2-isocyanatoethyl methacrylate in 50 ml of methylene chloride was allowed to stand at room temperature for 4 days. The reaction mixture was then washed with 5% sodium carbonate, water, and dried with MgSO$_4$. After filtering, the solvent was removed under reduced pressure by means of a rotary evaporator to give 3.35 g of the dimethacrylate derivative as a viscous oil having a λmax of 254 nm. The structural formula of the product is as follows:

Example 19

This example illustrates the preparation of a methacrylate derivative of a trichloromethyl-1,3,5-triazine compound by means of the cotrimerization of an aromatic nitrile and trichloroacetonitrile. A solution of 5.0 g of 3-cyanophenol, 6.5 g of 2-isocyanatoethyl methacrylate, and 3 drops of di-n-butyltin dilaurate in 50 ml of methylene chloride was allowed to stand at room temperature for 24 hours. The solution was washed with 20% Na$_2$CO$_3$, saturated NaCl, dried with MgSO$_4$, and concentrated to give 10.1 g of N-(2-ethylmethacrylate)-(3-cyanophenyl)carbamate having a melting point of 69°–71° C.

To a glass pressure vessel was added 2.74 g of the above carbamate, 2.89 g of trichloroacetonitrile, 10 mg of zinc chloride, and 5 ml of methylene chloride. The vessel was connected to a hydrogen chloride cylinder, and then cooled in an acetone-dry ice bath. Hydrogen chloride was added and the system allowed to purge. Upon sealing, a pressure of 20 psi was maintained for one hour; the cooling bath was then removed, and the system was warmed to room temperature. The pressure was raised to 50 psi in the vessel, which was allowed to stand for 5 days. The vessel was opened and 100 ml of methylene chloride added. This solution was extracted with water, dried with MgSO$_4$, and concentrated to give 4.9 g of a viscous oil. When triturated with hexane-methanol a waxy solid formed slowly. Recrystallization with methanol gave the desired product. The product had a melting point of 118°–119° C. and a λmax of 278 nm. The structural formula of the product is as follows:

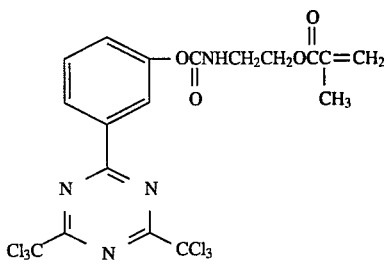

EXAMPLES 20–23

These examples illustrate the preparation of copolymers by using methacrylate derivatives of trichloromethyl-1,3,5-triazine compounds.

Example 20

One part by weight of a triazine monomer (the product of Example 2), nine parts by weight of a co-monomer (isooctyl acrylate), and 0.005 part by weight of azobisisobutyronitrile were dissolved in 15 parts by weight of ethyl acetate and the solution was purged with nitrogen for two to three minutes. The container was capped, placed in a water bath at 50°–55° C., and agitated for approximately 20–24 hours. The viscosity of the solution increased and the infrared spectrum of the film forming product showed the disappearance of vinyl monomer. Samples of the polymers were analyzed in a Hewlett Packard 1090 Liquid Chromatograph equipped with a Series L diode array detector and a PLgel 10 micron "mixed" bed column using tetrahydrofuran as the solvent. The elution of the polymer with tetrahydrofuran was followed using the ultraviolet/visible light diode array detector. The spectroscopic data showed that the triazine chromophore was incorporated throughout the polymer. The polymer was isolated from the reaction solution by precipitation with hexane or by evaporation of the solvent. The structural formula of the product is as follows:

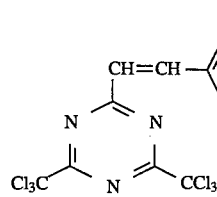

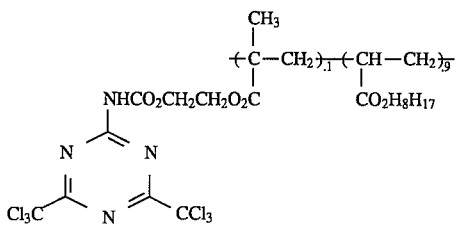

Example 21

The procedure of Example 20 was repeated with the exceptions being that methyl methacrylate was used instead of isooctyl acrylate and that the product of Example 12 was used instead of the product of Example 2. The structural formula of the product is as follows:

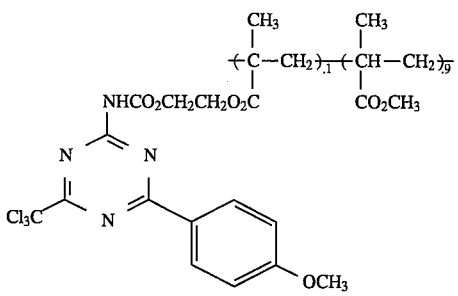

Example 22

The procedure of Example 20 was repeated with the exceptions being that eight parts by weight of methyl methacrylate was used instead of isooctyl acrylate and that two parts by weight of the product of Example 15 was used instead of the product of Example 2. The structural formula of the product is as follows:

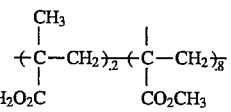

Example 23

The procedure of Example 20 was repeated with the exception being that the product of Example 19 was used instead of the product of Example 2. The structural formula of the product is as follows:

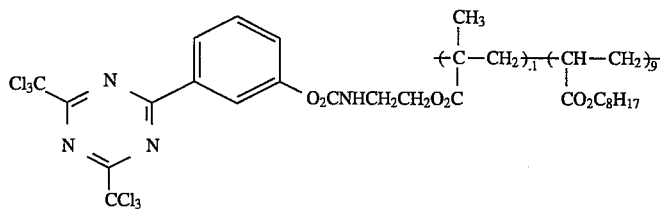

Example 24

This example illustrates the use of the compounds of this invention in light-sensitive coatings. A solution was prepared from 74.24 g azeotrope of 1-propanol and water (71.8% 1-propanol/28.2% water), 4.32 g pentaerythritol tetraacrylate ("Sartomer" monomer SR-295, Arco Chemical Company), 5.64 g oligomer (prepared according to U.S. Pat. No. 4,228,232; 60.9% in methyl ethyl ketone), 0.30 g triethylamine, and 14.88 g a 1:1 mixture of polyvinyl acetate-methylal resin ("Formvar" 12/85T, Union Carbide Corp.) and red pigment (Pigment Red 48, C.I. 15865) (9.4% by weight solution of the azeotrope). To 2.5 g of this solution was added 2.5 mg dimethylaminobenzylacetone (DMBA), 10 mg initiator, and the resulting solution shaken in the dark for 15 minutes. The solution was then filtered through glass wool and coated onto a grained, anodized aluminum plate with a #12 Mayer bar. The plate was dried at 66° C. for 2 minutes and then cooled to room temperature. To this coating was applied a topcoat formulation (prepared from 5.00 g carboxymethyl cellulose ether (CMC-7L), 0.26 g surfactant ("Triton" X-100; 10% in water), and 95.00 g water) with a #14 Mayer bar and carefully dried with a heat gun. The plates were exposed for 5 seconds in air on top of a draw-down glass in a 3M Seventy exposure unit equipped with a 2 kw photopolymer bulb through a √2, 21 step Stouffer step tablet. The plates were soaked in a developer solution prepared from 784.4 g deionized water, 16.7 g sodium metasilicate pentahydrate, 33.4 g 1-propanol, and 0.5 g surfactant ("Dowfax-2A1", Dow Chemical Company) (45% solution in water) for 15 seconds and rubbed 10 times with a 4 in.×4 in. cotton pad. The relative sensitivities for the triazine compounds of Examples 1–5, 7–11 are shown in Table 2.

TABLE 2

| Initiator | Solid step no. |
|---|---|
| Example 1 | 12 |
| Example 2 | 13 |
| Example 3 | 6 |
| Example 4 | 6 |
| Example 5 | 13 |
| Example 7 | 13 |
| Example 8 | 11 |
| Example 9 | 12 |
| Example 10 | 10 |
| Example 11 | 11 |

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A radiation-sensitive composition comprising: (1) an ethylenically unsaturated, polymerizable compound, and (2) a compound having at least one halomethyl substituent attached to a carbon atom on a triazine nucleus and at least one polymerizable monomeric moiety attached to a different carbon atom of the triazine nucleus, said polymerizable monomeric moiety being capable of free radical or ionic chain polymerization.

2. A radiation-sensitive composition comprising: (1) an ethylenically unsaturated, polymerizable compound, and (2) a compound having the formula:

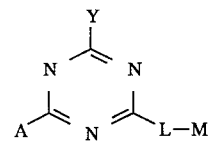

wherein
A represents a member selected from the group consisting of mono-, di- and trihalomethyl groups, Y represents a member selected from the group consisting of A, L—M, $NH_2$, NHR, $NR_2$, OR, and R', where R independently represents a member selected from the group consisting of substituted and unsubstituted alkyl groups, and substituted and unsubstituted aryl groups, and R' represents a member selected from the group consisting of substituted and unsubstituted alkyl groups, substituted and unsubstituted aryl groups, substituted and unsubstituted alkenyl groups, substituted and unsubstituted polyalkenyl groups, substituted and unsubstituted alkynyl groups, substituted and unsubstituted polyalkynyl groups, and substituted and unsubstituted heteroaromatic groups, M represents at least one monomeric moiety capable of undergoing free radical or ionic chain polymerization, and L represents a group or a covalent bond linking the monomeric moiety to the triazine nucleus.

3. The composition of claim 1, wherein said at least one halomethyl group is a trihalomethyl group.

4. The composition of claim 3, wherein said trihalomethyl group is a member selected from the group consisting of trichloromethyl group, tribromomethyl group, and triiodomethyl group.

5. The composition of claim 1, wherein said monomeric moiety is selected from the group consisting of acrylate group, methacrylate group, acrylamide group, vinyl ether group, allyl ether group, epoxide group, and allyl amine group.

6. The composition of claim 2, wherein A represents a trihalomethyl group.

7. The composition of claim 6, wherein the trihalomethyl group is a member selected from the group consisting of trichloromethyl, tribromomethyl, and triiodomethyl.

8. The composition of claim 7, wherein the trihalomethyl group is a member selected from the group consisting of trichloromethyl and tribromomethyl.

9. The composition of claim 2, wherein M represents a monomeric moiety selected from the group consisting of acrylate group, methacrylate group, acrylamide group, vinyl ether group, allyl ether group, epoxide group, and allyl amine group.

10. The composition of claim 2, wherein Y represents A.

11. The composition of claim 2, wherein Y represents L—M.

12. The composition of claim 2, wherein R' represents a substituted or unsubstituted aryl group.

13. The composition of claim 2, wherein R' represents a substituted or unsubstituted heterocyclic aromatic group.

14. The composition of claim 2, wherein R' represents a substituted or unsubstituted alkenyl group.

15. The composition of claim 2, wherein R' represents a substituted or unsubstituted alkynyl group.

* * * * *

UNITED STATES PATENT AND TRADEMARK OFFICE
CERTIFICATE OF CORRECTION

PATENT NO.: 5,496,504

DATED: March 5, 1996

INVENTOR(S): James A. Bonham, Mitchell A. Rossman, Richard J. Grant

It is certified that error appears in the above-identified patent and that said Letters Patent is hereby corrected as shown below:

Column 25, line 59, mononaeric should read monomeric

Signed and Sealed this

Twenty-fifth Day of March, 1997

Attest:

BRUCE LEHMAN

Attesting Officer

Commissioner of Patents and Trademarks